US009693947B1

(12) United States Patent
Marini et al.

(10) Patent No.: US 9,693,947 B1
(45) Date of Patent: Jul. 4, 2017

(54) HYLA3D HYLAURONIC ACID ACTIVATING COMPLEX

(71) Applicant: Jan Marini Skin Research, San Jose, CA (US)

(72) Inventors: Jan L. Marini, San Jose, CA (US); Subhash J. Saxena, Ringoes, NJ (US)

(73) Assignee: Jan Marini Skin Research, San Jose, CA (US)

( * ) Notice: Subject to any disclaimer, the term of this patent is extended or adjusted under 35 U.S.C. 154(b) by 0 days.

(21) Appl. No.: 15/424,480

(22) Filed: Feb. 3, 2017

(51) Int. Cl.
| | |
|---|---|
| *A61K 8/73* | (2006.01) |
| *A61K 8/11* | (2006.01) |
| *A61K 8/60* | (2006.01) |
| *A61K 8/35* | (2006.01) |
| *A61K 8/64* | (2006.01) |
| *A61K 8/06* | (2006.01) |
| *A61K 8/55* | (2006.01) |
| *A61K 8/04* | (2006.01) |
| *A61Q 19/08* | (2006.01) |

(52) U.S. Cl.
CPC .............. *A61K 8/735* (2013.01); *A61K 8/042* (2013.01); *A61K 8/06* (2013.01); *A61K 8/11* (2013.01); *A61K 8/355* (2013.01); *A61K 8/553* (2013.01); *A61K 8/60* (2013.01); *A61K 8/64* (2013.01); *A61Q 19/08* (2013.01); *A61K 2800/594* (2013.01)

(58) Field of Classification Search
None
See application file for complete search history.

(56) References Cited

U.S. PATENT DOCUMENTS

2006/0292086 A1\* 12/2006 Curtis .................... A61K 8/046
424/47

FOREIGN PATENT DOCUMENTS

CN             101450028 A    \*  6/2009

\* cited by examiner

*Primary Examiner* — Carlos Azpuru
*Assistant Examiner* — Casey Hagopian
(74) *Attorney, Agent, or Firm* — Pamela J. Sherwood; Bozicevic, Field & Francis LLP

(57) ABSTRACT

The present invention provides cosmetic formulations for improving the appearance of the skin, including the facial area. The compositions of the invention provide multiple enhanced technologies that work synergistically to enhance hydration and appearance of the skin. Anti-aging peptides and tissue respiratory factor work together in an HA rich environment to enhance collagen and elastin while beneficial antioxidants protect HA in the skin from damaging exposure.

12 Claims, 2 Drawing Sheets
(2 of 2 Drawing Sheet(s) Filed in Color)

HYLA3D HYLAURONIC ACID ACTIVATING COMPLEX

BACKGROUND

Human skin aging is a multifactorial and complex biological process affecting the different constituents of the skin. Skin aging is a combination of intrinsic or innate aging, and extrinsic aging (or photoaging) that results from exposure to environmental factors such as sunlight, pollutants, etc.

With age—skin volume, resilience, and pliability are decreased, at least in part due to altered patterns and levels of glycosaminoglycans (GAGs), especially hyaluronic acid (HA). Glycosaminoglycans and proteoglycans are abundant structural components of the extracellular matrix in addition to collagen fibers. HA forms large complexes that crosslink to other matrix proteins, such as collagen, resulting in the formation of supermolecular structures and functions to provide structure to the skin. HA has a unique capacity to bind and retain water molecules. Chemically, HA is composed of repeating polymeric disaccharides of D-glucuronic acid and N-acetyl-D-glucosamine linked by a glucuronidic β (1→3) bond. Unlike other GAGs, HA is not covalently linked to a protein core, but it may form aggregates with proteoglycans. HA polymers occur in a large number of configurations and shapes, depending on their size, salt concentration, pH, and associated cations.

In humans, HA is most abundant in the skin. The most dramatic histochemical change observed in senescent skin is the marked disappearance of epidermal HA. With increasing aging, a steady decline of HA occurs in the upper epidermal layer, with concomitant increases in the basal layer of the epidermis and the upper portions of the papillary dermis, while at senescence HA is entirely absent in the epidermis and present in the upper dermis. It is evident that during aging the epidermis loses the principal molecule responsible for binding and retaining water molecules, resulting in loss of skin moisture and accounting for some of the most striking alterations of the aged skin, including decreased structure, less support for microvessels, wrinkling, altered elasticity and loss of face volumes especially as regards to the cheekbones and lips.

The cosmetic formulation of the invention address specific needs of aging skin.

SUMMARY OF THE INVENTION

The present invention provides cosmetic formulations for improving the appearance of the skin, including the facial area. The compositions of the invention provide multiple enhanced technologies that work synergistically to enhance hydration and appearance of the skin. Anti-aging peptides and tissue respiratory factor work together in an HA rich environment to enhance collagen and elastin while beneficial antioxidants protect HA in the skin from damaging exposure.

According to the first aspect of the invention, there is provided a cosmetic composition comprising a specific and efficacious blend of agents. The agents include multiple forms of HA; agents that enhance endogenous HA, and agents that boost collagen and elastin. The multiple forms of HA comprise: liposomal encapsulated HA, which enhances delivery of large molecular weight HA deep into the skin; time-release cross-linked HA for consistent, long-term hydration; ultra-low molecular weight HA for deep delivery; and traditional HA for immediate hydration. Agents that boost enhance endogenous HA and boost collagen and elastin comprise Coenzyme Q10; HA peptide, HA booster and Dermal Respiratory Factor.

In the second aspect of the invention, a method is provided for improving the appearance of the skin, in particular to improve skin tone, texture and luminosity, the method comprising applying topically a cosmetic lotion composition comprising an efficacious blend of multiple forms of HA comprising liposomal encapsulated HA; cross-linked HA; ultra-low molecular weight HA; and traditional HA; and agents that boost enhance endogenous HA and boost collagen and elastin comprising Coenzyme Q10; HA peptide (oligopeptide-24), HA booster and Dermal Respiratory Factor.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE EMBODIMENTS

Figure 1A:
FIG. 1A-1B show the results of use of HYLA3D activating complex. The lotion was applied twice daily for one month FIG. 1A and for 2 months FIG. 1B. The results show a dramatic change in skin appearance after regular use of the product.

The cosmetic formulations improve the appearance of signs of aging, including softening the appearance of deep wrinkles and creases; reducing the appearance of fine lines; and improving texture of the skin. The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders. The cosmetically acceptable vehicle will usually form 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifier and co emulsifier may be present in the composition at a proportion ranging from 0.3% to 30% by weight, and preferably from 0.5% to 20% by weight, relative to the total weight of the composition.

The compositions may be in the form of an aqueous serum or gel. These compositions are formulated according to the usual techniques as are well known to this art. The compositions of the invention may further comprise cosmetically useful agents and excipients, e.g. glycerin, cetyl alcohol, capric triglyceride, glyceryl stearate, PEG-100 stearate, steareth-20, steareth-2, cyclopentasiloxane, phenoxyethanol, lecithin, tocopherol, aloe vera, etc. each at a concentration of from about 0.1% to about 10% by weight, usually from about 0.5% to about 5%, and may be present at a concentration of from about 0.5%, 1%, 2%, 3%, 4%, 5%, etc.

Components of the Cosmetic Compositions

The compositions of the invention comprise a specific blend of therapeutic agents, including the following agents.

Forms of Hyaluronic Acid

Liposomal HA.

Liposomal HA contains liposomally encapsulated sodium hyaluronate, which is delivered through the lipid barrier to the deeper skin layers. The product is commercially available, for example from Air Products and Chemicals, Inc., as ROVISOME®. The HA may be encapsulated, for example in lecithin, in an aqueous/alcohol diluent. In such compositions, the HA may be about 0.5% by weight, lecithin about 17.5% by weight, and the balance diluent.

The concentration of encapsulated liposomal HA may be represented in the formulation of the invention as the fraction of HA in the encapsulate, or as the finished formula concentration of the liposomal composition. When expressed as the liposomal composition, the liposomal HA may be present at a concentration of at least about 0.5%; at least about 1%; and not more than about 5%, not more than about 3%; and may be present at about 2% of the formula weight. It will be understood by one of skill in the art that the liposomal formulation comprises HA and other excipients.

Cross-Linked HA.

Crosslinked hyaluronic acid (CAS 105524-32-1) is a polymer of HA crosslinked with vinylsulfone. It has a high water-binding capacity, and is a scavenger of damaging free radicals. The polymer forms a film on the skin that is broken down over time, allowing for a sustained release of HA to the skin. Suitable compositions are commercially available, e.g. Hylasome® EG10, from Lipo Chemicals, Inc.

The concentration of cross-linked HA may be represented as a percentage of formula weight, and may be present at a concentration of at least 0.25%, at least 0.5%, and not more than about 3%, not more than about 2%; and may be present at about 1% of the formula weight.

Ultra Low Molecular Weight HA.

Hyaluronic Acid ULMW (CAS 9067-32-7) is enzymatically cleaved to have a molecular weight of less than about 6 kD. The low molecular weight reduces its viscosity in water, but improves its ability to penetrate the upper layers of the skin. Suitable composition are commercially available, for example Hyaluronic Acid ULMW, from Lotioncrafter LLC.

The concentration of ULMW HA may be represented as a percentage of formula weight, and may be present at a concentration of at least 0.25%, at least 0.5%, and not more than about 3%, not more than about 2%; and may be present at about 1% of the formula weight.

Traditional HA.

Sodium hyaluronate (CAS 9067-32-7) is an anionic, nonsulfated glycosaminoglycan distributed widely throughout connective, epithelial, and neural tissues, and can be produced by natural fermentation and purification processes. It is a natural humectant. The native forms of the polymer can be very high molecular weight, for example greater than 100 kD, greater than 500 kD, greater than 1000 kD. Compositions are widely available for example from Lifecore Biomedical; TRI-K Industries, Inc.; Centerchem; and others.

The concentration of HA may be represented as a percentage of formula weight, and may be present at a concentration of at least 0.0025%, at least 0.005%, and not more than about 0.1%, not more than about 0.05%; and may be present at about 0.01% of the formula weight.

Activating Agents

Calcium Ketogluconate (HA Booster).

Gluconic acid, which can be derived from glucose, may be further oxidized to form ketogluconate (D-Arabino-2-hexulosonic acid, CAS 28098-92-2). Methods of synthesis and use are known in the art, for example see US Patent application number: 20120015012; and Pfeifer et al. (1958) *Ind. Eng. Chem.* 50 (7):1009-1012. It has been reported to stimulate hyaluronic acid and/or elastin synthesis in the dermis. Compositions of calcium ketogluconate can be produced and isolated by methods known in the art, or are commercially available, e.g. Stimulhyal® from Soliance.

The concentration of calcium ketogluconate may be represented as a percentage of formula weight, and may be present at a concentration of at least 0.1%, at least 0.25%, and not more than about 2%, not more than about 1%; and may be present at about 0.5% of the formula weight.

Ubiquinone, Coenzyme Q10.

Coenzyme Q10 (CAS 303-98-0), also known as ubiquinone, is a coenzyme that is ubiquitous in the bodies of most animals. It is a 1,4-benzoquinone, where Q refers to the quinone chemical group and 10 refers to the number of isoprenyl chemical subunits in its tail. This fat-soluble substance is a component of the electron transport chain and participates in aerobic cellular respiration. Ubiquinone naturally decreases with aging, and provides an anti-aging ingredient that replaces some of the natural antioxidant produced by the body. When applied topically, ubiquinone penetrates the skin easily, and reduce free radical damage via its antioxidant properties. Compositions of ubiquinone are widely available.

The concentration of ubiquinone may be represented as a percentage of formula weight, and may be present at a concentration of at least 0.05%, at least 0.1%, and not more than about 2%, not more than about 1%; not more than about 0.5%; and may be present at about 0.2% of the formula weight.

In some embodiments, ubiquinone is provided in a phospholipid emulsion system, which accelerates the effects of active ingredients and allows them to penetrate the skin upon dermal application. Highly concentrated solutions of polyols (e.g. glycerol, sorbitol) and phospholipds facilitate the dissolution of large quantity of lipids and form transparent to translucent emulsions of honey-like to gel-like consistency and with droplet sizes of less than 100 nm. Such formulations are commercially available, for example PhytoSolve® 4037, available from Lipoid LLC. When ubiquinone is provided in such a formulation, the formulation may be present at a concentration of at least about 0.25%, at least about 0.5%, and not more than about 3%, not more than about 2%, and may be present at about 1% of the formula weight.

Dermal Respiratory Factor.

Dermal respiratory factor (Code Number: 20219PF INCI Name: Water & *Saccharomyces* Lysate Extract) comprises *Saccharomyces* cell derivative (LYCD) and *Lactobacillus* ferment. LYCD is produced when live yeast cells are exposed to stress, such as UV radiation. This yields a material which has shown to stimulate cellular metabolism by promoting the increase of cellular energy. LCYD is primarily used to stimulate oxygen consumption, combat irritation, or as a cosmetic potentiator. It has been reported to promote collagen and elastin synthesis. A commercially available source is AC Dermal Respiratory Factor Advanced PF, from Active Concepts LLC. In the composition, yeast extract is present at a concentration of 24%, and *lactobacillus* at a concentration of 2%.

The concentration of active agent may be represented in the formulation of the invention as the fraction of LYCD, or as the finished formula concentration of the Dermal Respiratory Factor composition. When expressed as the concentration of Dermal Respiratory Factor formulation present in the cosmetic formulation of the invention, the respiratory factor may be present at a concentration of at least about 0.25%; at least about 0.5%; and not more than about 5%, not more than about 3%; and may be present at about 1% of the formula weight. It will be understood by one of skill in the art that the Dermal Respiratory Factor formulation comprises aqueous diluents in addition to the microbial cell extracts.

HA Peptide.

Oligopeptide-24 is an oligopeptide reported to upregulate expression of elastin and hyaluronic acid, and to increase fibroblast activity. The oligopeptide is provided in a double layered encapsulation formulation as CD-EDP3, from Caregen.

When expressed as the level of oligopeptide itself in a formulation of the invention, the oligopeptide 24 may be represented as a percentage of formula weight, and may be present at a concentration of at least 0.00025%, at least 0.0005%, and not more than about 0.01%, not more than about 0.005%; and may be present at about 0.001% of the formula weight.

The amounts of cosmetic or dermatological auxiliaries and additives and perfume to be used in each case can easily be determined by simple exploratory experiments by the person skilled in the art, depending on the nature of the product in question. Preferably the compositions of the invention are fragrance free and paraben-free.

Cosmetically Acceptable Vehicle

The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders.

The compositions of the invention include a cosmetically acceptable vehicle to act as a diluent, dispersant or carrier for the active agents, so as to facilitate distribution and uptake when the composition is applied as a lotion. Vehicles other than or in addition to water, triglycerides, glycerol, etc. can include liquid or solid emollients, solvents, humectants, thickeners and powders. The cosmetically acceptable vehicle will usually form 5% to 99.9%, preferably from 25% to 80%, about 40% to 60%, by weight of the composition, and can, in the absence of other cosmetic adjuncts, form the balance of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Accordingly, a composition of the invention comprises a lotion with skin lightening agents, retinol, epigallocatechin gallate and bisabolol in an emulsion suitable for administration as a lotion. Furthermore, a composition of the invention may include additional agents or additives that are not in themselves active agents but play a role in promoting the usefulness or effectiveness of an active agent.

Compositions of the invention may be applied to any subject and used to treat a variety of conditions, particularly for the reducing the appearance of spots and discoloration, reducing the appearance of redness, brightening skin and reducing the appearance of fine lines and wrinkles. A typical composition of the invention is formulated as a lotion, which may be applied topically once or twice daily.

Product Use, Form, and Packaging

In use, a quantity of the composition, for example from 1 to 100 ml, is applied to a site of interest from a suitable container or applicator and, if necessary, it is then spread over and/or rubbed into the site using the hand or fingers or a suitable device. The product may be specifically formulated for use as a treatment for a specific area, e.g. the neck, the face, etc.

The cosmetic composition of the invention can be formulated in any form suitable for application to the site of interest, including a lotion, cream, gel, or the like. The composition can be packaged in any suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLE 1

Example 1 illustrates a topical composition according to the present invention. The composition can be processed in conventional manner and is suitable for cosmetic use. In particular the compositions are suitable for application to a site of interest for the treatment of a variety of skin conditions.

| HYLA3D Complex | | |
|---|---|---|
| CAS number | Name | Final concentration |
| | Encapsulated, high molecular weight Sodium Hyaluronate | 0.5%-5% |
| 105524-32-1 | Sodium Hyaluronate Crosspolymer | 0.25%-3% |
| 9067-32-7 | Ultra Low Molecular Weight Sodium Hyaluronate | 0.25%-3% |
| 9067-32-7 | Traditional Sodium Hyaluronate | 0.0025%-0.05% |
| 8013-01-2; 68333-16-4 | AC Dermal Respiratory Factor | 0.25%-5% |
| 28098-92-2 | Calcium Ketogluconate (HA booster) | 0.1%-2% |
| 303-98-0 | Ubiquinone (CoEnzyme Q10) | 0.5%-2% |
| | CG-EDP3 Encapsulated Solution (Oligopeptide -24) | 0.00025%-0.01% |

Additional ingredients can be included to provide a cosmetically acceptable vehicle and to bring the volume to 100%, comprising one or more of water, C10-30 Alkyl Acrylate Crosspolymer; Alcohol; Butylene Glycol; Caprylic/Capric Triglyceride; Caprylyl Glycol; Citric Acid; Dimethicone/Vinyl Dimethicone Crosspolymer; Disodium EDTA; DL-Panthenol 50L; Ethylhexylglycerin; Glycerin; Soybean Oil; Hexylene Glycol; Isoceteth-10; Lecithin; Panthenol; Pentylene Glycol; *Peucedanum Graveolens* (Dill) Extract; Phenoxyethanol; Potassium Phosphate; Silica; Sodium Oleate; Tocopherol; and Xanthan Gum.

Figure 1B:

As shown in FIG. 1, twice daily use of the topical composition over a period of from 1 to 2 months provides for improved appearance of the skin.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cosmetic composition for topical application to improve appearance of skin comprising:
   a blend of hyaluronate forms comprising:
   0.5% to 5% by weight encapsulated sodium hyaluronate; 0.25% to 3% by weight sodium hyaluronate crosspolymer; 0.25% to 3% by weight ultra low molecular weight sodium hyaluronate; and 0.0025% to 0.05% by weight high molecular weight sodium hyaluronate; and
   a cosmetically acceptable vehicle.

2. The composition of claim 1, further comprising a blend of activating ingredients comprising:
   0.25% to 5% by weight dermal respiratory factor formulation; 0.1% to 2% by weight calcium ketogluconate;

0.5% to 2% by weight ubiquinone; and 0.00025%-0.01% by weight oligopeptide-24.

3. The composition of claim 1 wherein the blend of hyaluronate forms comprises:

1% to 3% by weight encapsulated sodium hyaluronate; 0.5% to 2% by weight sodium hyaluronate crosspolymer; 0.5% to 2% by weight ultra low molecular weight sodium hyaluronate; and 0.005% to 0.05% by weight high molecular weight sodium hyaluronate.

4. The composition of claim 3, wherein the blend of activating ingredients comprises:

0.5% to 3% by weight dermal respiratory factor formulation; 0.25% to 1% by weight calcium ketogluconate; 0.1% to 1% by weight ubiquinone; and 0.0005%-0.005% by weight oligopeptide-24.

5. The composition of claim 4, wherein the ubiquinone is provided in a phospholipid emulsion.

6. The composition of claim 4, formulated as a serum or gel.

7. A method of improving the appearance of the skin, comprising:

topically applying a cosmetic formulation comprising a blend of hyaluronate forms comprising:

0.5% to 5% by weight encapsulated sodium hyaluronate; 0.25% to 3% by weight sodium hyaluronate crosspolymer; 0.25% to 3% by weight ultra low molecular weight sodium hyaluronate; and 0.0025% to 0.05% by weight high molecular weight sodium hyaluronate; and a cosmetically acceptable vehicle.

8. The method of claim 7, wherein the cosmetic formulation further comprises:

a blend of activating ingredients comprising:

0.25% to 5% by weight dermal respiratory factor formulation; 0.1% to 2% by weight calcium ketogluconate; 0.5% to 2% by weight ubiquinone; and 0.00025%-0.01% by weight oligopeptide-24.

9. The method of claim 7, wherein the blend of hyaluronate forms comprises:

1% to 3% by weight encapsulated sodium hyaluronate; 0.5% to 2% by weight sodium hyaluronate crosspolymer; 0.5% to 2% by weight ultra low molecular weight sodium hyaluronate; and 0.005% to 0.05% by weight high molecular weight sodium hyaluronate.

10. The method of claim 8, wherein the blend of activating ingredients comprises:

0.5% to 3% by weight dermal respiratory factor formulation; 0.25% to 1% by weight calcium ketogluconate; 0.1% to 1% by weight ubiquinone; and 0.0005%-0.005% by weight oligopeptide 24.

11. The method of claim 10, wherein the ubiquinone is provided in a phospholipid emulsion.

12. The method of claim 10, wherein the cosmetic formulation is a serum or gel.

* * * * *